United States Patent [19]

Eastburg

[11] 4,271,181

[45] Jun. 2, 1981

[54] SYNERGISTIC INSECTICIDAL COMBINATIONS COMPRISING ENDOSULFAN AND 2-DIHALOVINYL-3,3-DIMETHYLCYCLOPROPANECARBOXYLATES

[75] Inventor: Paul H. Eastburg, Cherry Hill, N.J.

[73] Assignee: FMC Corporation, Philadelphia, Pa.

[21] Appl. No.: 753,040

[22] Filed: Dec. 22, 1976

[51] Int. Cl.$^3$ .................... A01N 43/24; A01N 37/00; A01N 37/08; A01N 37/06

[52] U.S. Cl. .................................. 424/276; 424/306; 424/314

[58] Field of Search .................. 424/276, 314, 306

[56] References Cited

U.S. PATENT DOCUMENTS

| | | | |
|---|---|---|---|
| 2,799,685 | 7/1957 | Frensch et al. | 424/276 |
| 3,358,011 | 12/1967 | Elliott | 424/311 |
| 3,885,031 | 5/1975 | Montgomery et al. | 424/172 |
| 3,944,666 | 3/1976 | Montgomery et al. | 424/219 |
| 4,210,642 | 7/1980 | Bock et al. | 424/200 |

FOREIGN PATENT DOCUMENTS

| | | | |
|---|---|---|---|
| 1150242 | 6/1963 | Fed. Rep. of Germany | 424/311 |
| 2001300 | 11/1970 | Fed. Rep. of Germany | 424/276 |
| 2109020 | 5/1972 | France | 424/276 |
| 1413491 | 11/1975 | United Kingdom . | |

*Primary Examiner*—Douglas W. Robinson
*Attorney, Agent, or Firm*—Richard L. Hansen; Henry R. Ertelt

[57] ABSTRACT

Compositions comprising, in combination, the insecticides endosulfan and 2-dihalovinyl-3,3-dimethylcyclopropanecarboxylates exhibit synergistic insecticidal activity. The novel compositions are exemplified and their use for controlling insects is demonstrated.

5 Claims, No Drawings

SYNERGISTIC INSECTICIDAL COMBINATIONS COMPRISING ENDOSULFAN AND 2-DIHALOVINYL-3,3-DIMETHYLCYCLOPROPANECARBOXYLATES

BACKGROUND OF THE INVENTION

1. Field of the Invention

This invention pertains to the field of bio-affecting compositions; more specifically, it pertains to such compositions containing organic active ingredients comprising the insecticide endosulfan and certain esters of 2-dihalovinyl-3,3-dimethylcyclopropane carboxylic acids, the latter being pyrethroid insecticides related to chrysanthemum acid, and to the use of the compositions for controlling insects.

2. Description of the Prior Art

New pyrethroids, insecticidal 2-(2,2-dihalovinyl)-3,3-dimethylcyclopropanecarboxylates [Elliott, et al., Nature, 246, 169(1973); British Patent No. 1,413,491], are of great interest currently because, unlike previous compounds of this type, such as natural pyrethrins and the older synthetic pyrethroids (for example, allethrin and tetramethrin) they have good photo-oxidative stability. However, the new pyrethroids are very costly, and ways to increase their cost effectiveness are actively being sought.

Synergists have been used commercially in combination with pyrethrins and the older pyrethroid insecticides because they lessen the amount of insecticide required and thus reduce the cost at which insect control is achieved. Some of the most widely used synergists for pyrethrins and the older pyrethroids display little or no insecticidal activity in their own right; for example, the commercially important piperonyl butoxide [U.S. Pat. No. 2,550,737] and certain phosphonates such as mono(alkyl and alkenyl) mono-$\omega$-alkynyl arylphosphonates [U.S. Pat. Nos. 3,885,031 and 3,944,666].

Some of the compounds which produce synergistic combinations with the new pyrethroid, 3-phenoxybenzyl 2-(2,2-dichlorovinyl)-3,3-dimethylcyclopropanecarboxylate, are themselves insecticides. It is known that combinations of 2-allyl-3-methylcyclopent-2-en-1-one-4-yl 2-(2,2-dimethylvinyl)-3,3-dimethylcyclopropanecarboxylate (allethrin) and N-(3,4,5,6-tetrahydrophthalimido)methyl 2-(2,2-dimethylvinyl)-3,3-dimethylcyclopropanecarboxylate (tetramethrin) with the aforesaid insecticidal 2-dihalovinyl-3,3-dimethylcyclopropanecarboxylate exhibit synergism when used to control several insect species, including insects of the order Diptera [U.S. Pat. No. 3,899,586]. O,O-Dimethyl O-(3-methyl-4-nitrophenyl)phosphorothioate (fenitrothion) and 1-naphthyl methylcarbamate (carbaryl), in combination with the aforesaid insecticidal 2-dihalovinyl-3,3-dimethylcyclopropanecarboxylate, exhibit synergism when applied to Nephetettix cinctceps, a rice pest [Japan Kokai Nos. 75 58,237 and 75 64,422, respectively].

Endosulfan, 6,7,8,9,10,10-hexachloro-1,5,5a,6,9,9a-hexahydro-6,9-methano-2,4,3-benzodioxathiepin-3-oxide, is known to produce synergistic insecticidal combinations with O,O-dimethyl O-(4-nitrophenyl)phosphorothioate (methyl parathion) and methyl 3[(dimethoxyphosphinyl)oxy]-2-butenoate (mevinphos) when employed against Agrotis segetum [Chem. Abstr., 82, 39465y (1975)]. When used to control Musca domestica, compositions comprising endosulfan in combination with 3-methyl-5-(1-methylethyl)-phenyl methylcarbamate (promecarb) or 2-chlorophenyl methylcarbamate exhibit synergism [Chem. Abstr., 80, 56490d (1974) and ibid., 78, 39357g (1973), respectively].

SUMMARY OF THE INVENTION

It has now been discovered that novel compositions of matter comprising endosulfan and at least one insecticidal 2-dihalovinyl-3,3-dimethylcyclopropanecarboxylate, such as 3-phenoxybenzyl 2-(2,2-dichlorovinyl)-3,3-dimethylcyclopropanecarboxylate, exhibit unexpectedly high insecticidal activity, 4-5 times higher than expected on the basis of simply additive activities.

As will be evident to those skilled in the art, formulated insecticides incorporating the aforesaid compositions may also contain the solvents, dispersants, surfactants, carriers and other adjuvants commonly employed in pesticides. The compositions may be formulated in many different ways, including aerosol and space sprays, wettable powders, granules, dusts, and flowable formulations.

Although the insecticidal activity of the aforesaid compositions may be enhanced if they contain as little as 10% endosulfan by weight, optimum synergism is obtained when the endosulfan/dihalovinylcyclopropanecarboxylate ratio is in the range 1/1 to 20/1.

Also within the contemplation of this invention is the use of the aforesaid novel compositions in a method for controlling insects. For example, the insecticidal compositions of this invention may be used to control insects of the order Diptera, exemplified by Musca domestica.

In using the novel compositions for controlling insects, it is only necessary to contact said insects with an insecticidally effective amount of a composition of this invention, preferably between about 100 and 1000 nanograms active ingredients per insect.

The nature of these novel compositions and their use for controlling insects will become more evident by reference to the following nonlimiting Examples.

DETAILED DESCRIPTION OF THE INVENTION

Between 0.4 $\mu l$ and 1.0 $\mu l$ of an acetone solution containing either commercial endosulfan (A), 3-phenoxybenzyl 2-(2,2-dichlorovinyl)-3,3-dimethylcyclopropanecarboxylate (B), whose preparation has been described [Elliott, et al., Nature, 246, 169 (1973); British Pat. No. 1 413 491], or a combination, designated (C), of 10 parts (A) per 1 part (B) by weight was applied topically to resistant, female house flies (Musca domestica, standard CSMA F58W-T strain). Counts of dead flies were made 24 hours later, and $LD_{50}$ was determined by standard probit analysis. The results were as follows:

| Dosage | (nanograms/fly) | | Number of Flies | | Mortality |
|---|---|---|---|---|---|
| (A) | (B) | (C) | Treated | Dead | (percent) |
| 200 | | | 84 | 43 | 51.2 |
| 300 | | | 85 | 65 | 76.5 |
| 400 | | | 82 | 79 | 96.3 |
| 500 | | | 83 | 83 | 100 |
| | 40 | | 81 | 15 | 18.5 |
| | 60 | | 80 | 41 | 51.3 |
| | 80 | | 86 | 60 | 69.8 |
| | 100 | | 88 | 77 | 87.5 |
| ( 80 + | 8 | ) = 88 | 92 | 16 | 17.4 |
| ( 120 + | 12 | ) = 132 | 81 | 38 | 46.9 |
| ( 160 + | 16 | ) = 176 | 84 | 60 | 71.4 |

-continued

| Dosage (nanograms/fly) | | | Number of Flies | | Mortality |
|---|---|---|---|---|---|
| (A) | (B) | (C) | Treated | Dead | (percent) |
| ( 200 | + 20 | ) = 220 | 84 | 69 | 82.1 |

$LD_{50}$ for (A) = 205 nanograms/fly
$LD_{50}$ for (B) = 60 nanograms/fly
$LD_{50}$ for (C) = 125 nanograms (A) + 12 nanograms (B)/fly

I claim:

1. A synergistic insecticidal composition consisting essentially of about 10 parts endosulfan per 1 part 3-phenoxybenzyl 2-(2,2-dichlorovinyl)-3,3-dimethylcyclopropanecarboxylate.

2. A method of controlling insects of the order Diptera which comprises contacting said insects with an insecticidally effective amount of a composition of claim 1.

3. The method of claim 2 wherein the insects are *Musca domestica*.

4. The method of claim 3 wherein contact is achieved by applying the composition to the insects.

5. The method of claim 4 wherein the insecticidally effective amount is between about 100 and 1,000 nanograms per insect.